(12) United States Patent
Stefinovic et al.

(10) Patent No.: US 9,725,454 B2
(45) Date of Patent: Aug. 8, 2017

(54) CRYSTALLINE FORMS OF PONATINIB HYDROCHLORIDE

(71) Applicant: SANDOZ AG, Basel (CH)

(72) Inventors: Marijan Stefinovic, Kundl (AT); Hayley Reece, Scotland (GB); Asha Sunkara, Scotland (GB)

(73) Assignee: SANDOZ AG, Basel (CH)

( * ) Notice: Subject to any disclaimer, the term of this patent is extended or adjusted under 35 U.S.C. 154(b) by 0 days.

(21) Appl. No.: 14/902,790

(22) PCT Filed: Jul. 4, 2014

(86) PCT No.: PCT/EP2014/064358
§ 371 (c)(1),
(2) Date: Jan. 4, 2016

(87) PCT Pub. No.: WO2015/001098
PCT Pub. Date: Jan. 8, 2015

(65) Prior Publication Data
US 2016/0297821 A1    Oct. 13, 2016

(30) Foreign Application Priority Data

Jul. 4, 2013   (EP) .................................... 13175184
Oct. 11, 2013  (EP) .................................... 13188348

(51) Int. Cl.
*C07D 487/04*   (2006.01)
*A61K 9/20*    (2006.01)

(52) U.S. Cl.
CPC .......... *C07D 487/04* (2013.01); *A61K 9/2009* (2013.01); *A61K 9/2018* (2013.01); *A61K 9/2054* (2013.01); *A61K 9/2059* (2013.01)

(58) Field of Classification Search
None
See application file for complete search history.

(56) References Cited

FOREIGN PATENT DOCUMENTS

| WO | WO 2007/075869 A2 | 7/2007 |
|---|---|---|
| WO | WO 2011/053938 A1 | 5/2011 |
| WO | WO 2014/093579 A2 | 6/2014 |
| WO | WO 2014/093583 A2 | 6/2014 |
| WO | WO 2015/085971 A1 | 6/2015 |
| WO | WO 2015/085972 A1 | 6/2015 |

OTHER PUBLICATIONS

International Search Report issued in PCT/EP2014/064358, mailed on Oct. 27, 2014.

*Primary Examiner* — Tigabu Kassa
(74) *Attorney, Agent, or Firm* — Arent Fox LLP (57) ABSTRACT

The present disclosure relates to polymorphic forms of the hydrochloride salt of ponatinib ("compound 1") and to processes for the preparation of these polymorphic forms. The present disclosure also generally relates to a pharmaceutical composition comprising the forms, as well of methods of using the form(s) in the treatment of disorders associated with pathological cellular proliferation, such as neoplasms, and cancer.

13 Claims, 3 Drawing Sheets

CRYSTALLINE FORMS OF PONATINIB HYDROCHLORIDE

CROSS-REFERENCE TO RELATED APPLICATIONS

This application is a National Stage entry of International Application No. PCT/EP2014/064358, filed Jul. 4, 2014, which claims priority to European Patent Application No. 13188348.0, filed Oct. 11, 2013, and European Patent Application No. 13175184.4, filed Jul. 4, 2013. The disclosures of the prior applications are hereby incorporated in their entirety by reference.

FIELD OF INDUSTRIAL APPLICABILITY

The present disclosure generally relates to polymorphic forms of the hydrochloride salt of ponatinib ("compound 1") and to processes for the preparation of these polymorphic forms. The present disclosure also generally relates to a pharmaceutical composition comprising the forms, as well of methods of using the form(s) in the treatment of disorders associated with pathological cellular proliferation, such as neoplasms, and cancer.

BACKGROUND OF THE DISCLOSURE

The compound ponatinib ("compound 1") is also known under the tradename Iclusig and was previously designated as AP24534. It is an FDA approved oral drug candidate developed by ARIAD Pharmaceuticals for the treatment of chronic myeloid leukemia (CML) and Philadelphia chromosome positive (Ph+) acute lymphoblastic leukemia (ALL). Generally speaking, the multi-kinase inhibitor is known to be useful in the treatment of disorders associated with pathological cellular proliferation, such as neoplasms, cancer, and conditions associated with pathological angiogenesis. The compound is a multi-target tyrosine-kinase inhibitor [W S Huang et al. (2010); Journal of Medical Chemistry 53 (12): 4701-19].

The compound was also designated as "3-(2-Imidazo[1,2-b]pyridazin-3-ylethynyl)-4-methyl-N-[4-[(4-methylpiperazine-1-yl)methyl]-3-(trifluoromethyl)phenyl]benzamide" or as "3-(imidazo[1,2-b]pyridazin-3-ylethynyl)-4-methyl-N-(4-((4-methylpiperazin-1-yl)-methyl)-3-(trifluoromethyl)phenyl)benzamide", depicted below:

Compound 1

The protein kinases are a large family of proteins which play a central role in the regulation of a wide variety of cellular processes. Abnormal protein kinase activity has been related to several disorders, ranging from non-life threatening diseases such as psoriasis to extremely serious diseases such as cancers. Several kinase inhibitors have been developed and used therapeutically with some important successes. However, not all of the targeted patients respond to those kinase inhibitors, and some become refractory to a given inhibitor through the emergence of mutation in the kinase or by other mechanisms.

The abnormal tyrosine kinase, BCR-ABL, is the hallmark of chronic myeloid leukemia (CML) and Philadelphia chromosome positive acute lymphoblastic leukemia (Ph+ ALL). Ponatinib is an oral, small-molecule pan-Bcr-Abl/Src protein inhibitor that is indicated in the US for the treatment of adults with chronic phase, accelerated phase, or blast phase chronic myeloid leukemia (CML) that is resistant or intolerant to prior tyrosine kinase inhibitor therapy, or Philadelphia chromosome positive acute lymphoblastic leukemia (Ph+ALL) that is resistant or intolerant to prior tyrosine kinase inhibitor therapy.

WO 2007/075869 A2 describes the synthesis of ponatinib (Example 16). Equivalent U.S. Pat. No. 8,114,874 is cited in the FDA Orange Book for ponatinib. WO 2011/053938 A1 claims an oral formulation comprising ponatinib which can be used for the treatment of neoplasms, cancers and hyperproliferative disorders e.g. chronic myelogenous leukemia (CML). The document also describes the synthesis of ponatinib and its mono hydrochloride salt (pages 42-44 of the document). According to the disclosure, the hydrochloride salt of ponatinib was found to be an anhydrous crystalline solid.

It has now been found that although many additional different solid state forms of ponatinib can be produced (by selecting appropriate conditions), only very few of the additional solid state forms show desirable characteristics for a pharmaceutical product. Moreover, for one particular form, form I, the present inventors found that it was not available in sufficient purity, e.g. polymorphic purity, when its preparation was approached by standard, solution-based crystallization processes.

The present invention therefore relates to solid state forms of ponatinib hydrochloride which possess advantageous physical properties. The solid state form and the associated properties can be influenced by controlling the conditions under which ponatinib hydrochloride is obtained in solid form.

Polymorphism, the occurrence of different crystal forms, is a property of some molecules and molecular complexes. A single molecule may give rise to a variety of polymorphs having distinct crystal structures and physical properties like melting point, thermal behaviors (e.g. measured by thermogravimetric analysis—"TGA", or differential scanning calorimetry—"DSC"), X-ray powder diffraction (XRPD or powder XRD) pattern, infrared absorption fingerprint, and solid state nuclear magnetic resonance (NMR) spectrum. One or more of these techniques may be used to distinguish different polymorphic forms of a compound.

Discovering new polymorphic forms and solvates of a pharmaceutical product can provide materials having desirable processing properties, such as ease of handling, ease of processing, storage stability, ease of purification or as desirable intermediate crystal forms that facilitate conversion to other polymorphic forms. New polymorphic forms and solvates of a pharmaceutically useful compound or salts thereof can also provide an opportunity to improve the performance characteristics of a pharmaceutical product. It enlarges the repertoire of materials that a formulation scientist has available for formulation optimization, for example by providing a product with different properties, e.g., better processing or handling characteristics, improved dissolution profile, improved stability, improved purity, or improved shelf-life.

Typically ponatinib hydrochloride is administered orally, as this route provides comfort and convenience of dosing. Although salts of ponatinib and polymorphic forms thereof are known in the art, finding a good or even the optimal form with regard to bioavailability, inter-patient variability, and safety remains a considerable challenge, in particular when the compound forms many salts or polymorphic forms. Further, not all forms of ponatinib are equally suitable with regard to polymorphic and chemical stability, flow properties, compressibility, dissolution rate, and some are at least to some extent hygroscopic or show electrostatic charging. These properties can constitute disadvantages in the preparation of pharmaceutical compositions, such as tablets.

It is therefore an object of the present invention to provide solid state forms of ponatinib hydrochloride, as well as pharmaceutical compositions comprising the same, which do not show at least one or more of the above-described problematic properties. In particular, it is an object to provide solid state forms of ponatinib hydrochloride which show good bioavailability, low inter-patient variability, excellent overall therapeutic efficacy, excellent polymorphic and/or chemical stability, excellent flow properties, good compressibility, an excellent dissolution profile, and which are non-hygroscopic and/or do not electrostatically charge. The present inventors have found a solid state form of ponatinib hydrochloride which shows advantageous properties in at least one of the mentioned aspects.

SUMMARY OF THE INVENTION

The present disclosure provides crystalline forms of ponatinib hydrochloride. Embodiments of these crystalline forms include those characterized herein as Form 1 and Form 8. The names used herein to characterize a specific form, e.g. "1" etc., should not be considered limiting with respect to any other substance possessing similar or identical physical and chemical characteristics, but rather it should be understood that these designations are mere identifiers that should be interpreted according to the characterization information also presented herein.

DETAILED DESCRIPTION OF THE INVENTION

The disclosure relates to crystalline forms of ponatinib hydrochloride, which are described and characterized herein.

Definitions

As used herein "polymorph" refers to crystalline forms having the same chemical composition but different spatial arrangements of the molecules, atoms, and/or ions forming the crystal.

As used herein "solvate" refers to a crystalline form of a molecule, atom, and/or ions that further comprises molecules of a solvent or solvents incorporated into the crystalline lattice structure. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate. Solvates may occur as dimers or oligomers comprising more than one molecule of ponatinib within the crystalline lattice structure.

As used herein "amorphous" refers to a solid form of a molecule, atom, and/or ions that is not crystalline. An amorphous solid does not display a definitive X-ray diffraction pattern.

As used herein, the term "substantially pure" with reference to a particular polymorphic form means that the polymorphic form includes less than 10%, preferably less than 5%, more preferably less than 3%, most preferably less than 1% by weight of any other physical forms of the compound.

Preparation of Crystalline Materials

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture.

Crystals of drugs, including polymorphs, methods of preparation, and characterization of drug crystals are discussed in *Solid-State Chemistry of Drugs*, S. R. Byrn, R. R. Pfeiffer, and J. G. Stowell, $2^{nd}$ Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science*, 1971, 26, 369-377. In general, seeds of small size are needed to control effectively the growth of crystals in the batch. Seed of small size may be generated by sieving, milling, or micronizing of large crystals, or by micro-crystallization of solutions. Care should be taken that milling or micronizing of crystals does not result in any change in crystallinity form the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, x-ray powder diffraction, or the like, to assure formation of the preferred crystalline form of the product. The product may be comilled or passed through a mesh screen to delump the product, if necessary.

Crystalline forms may be prepared directly from the reaction medium of the final process for preparing ponatinib. This may be achieved, for example, by employing in the final process step a solvent or a mixture of solvents from which ponatinib may be crystallized as its hydrochloride salt. Alternatively, crystalline forms may be obtained by distillation or solvent addition techniques. Suitable solvents for this purpose include, for example, the aforementioned nonpolar solvents and polar solvents, including protic polar solvents such as alcohols, and aprotic polar solvents such as ketones.

The present inventors have found that ponatinib hydrochloride form 1, when prepared directly from solutions of ponatinib hydrochloride in acetone, tetrahydrofuran, ethanol, ethyl acetate, methanol or acetonitrile/water by temperature cycling, consistently showed a relatively low degree of crystallinity. Upon drying, the obtained material was found to even decline in crystallinity.

Upon slurrying of ponatinib hydrochloride form 1 in water, crystal form conversion was observed. Briefly, form 1 of ponatinib hydrochloride had transformed to another form with a higher water content, which hereinafter is called form 8.

Surprisingly, when form 8 was isolated and then slurried in 2-propanol or acetone at 60° C., ponatinib hydrochloride form 1 was obtained again, but now with a higher degree of crystallinity than in the starting form 1. Without wishing to be bound to any theory, it appears that form 1 obtained from conversion of form 8 has a higher degree of crystallinity and is thus beneficial with respect to its suitability for pharmaceutical formulations. Moreover, form 1 obtained by conversion of form 8 contained a very low level of residual solvent, which is hard to remove by direct crystallization of form 1.

Various analytical methods may be used for characterization of crystalline ponatinib hydrochloride.

I. X-Ray Powder Diffraction Measurements

One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 5% or less, and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X- ray diffraction patterns substantially identical to those disclosed in the accompanying Figures fall within the scope of the present invention. The ability to ascertain substantial identities of X-ray diffraction patterns is within the purview of one of ordinary skill in the art.

X-Ray Powder Diffraction (XRPD)

XRPD analysis was carried out on a Siemens D5000, scanning the samples between 3° and 30° 2θ. For small sample amounts, the material was gently compressed onto a glass slide, fitted into an XRPD sample holder.

| Raw Data Origin | Siemens-binary V2 (.RAW) |
| --- | --- |
| Start Position [°2Th.] | 3.0000 |
| End Position [°2Th.] | 30.000 |
| Step Size [°2Th.] | 0.0200 |
| *Scan Step Time [s] | 1 |
| Scan Type | Continuous |
| Offset [°2Th.] | 0.0000 |
| Divergence Slit Type | Fixed |
| Divergence Slit Size [°] | 2.0000 |
| Specimen Length [mm] | various |
| Receiving Slit Size [mm] | 0.2000 |
| Measurement Temperature [° C.] | 20.00 |
| Anode Material | Cu |
| K-Alpha1/2 [Å] | 1.5419 |
| K-Beta [Å] | 1.39225 |
| K-A2/K-A1 Ratio | 0.50000 (nominal) |
| Generator Settings | 40 mA, 40 kV |
| Diffractometer Type | d5000 |
| Goniometer Radius [mm] | 217.50 |
| Incident Beam Monochromator | No |
| Diffracted Beam Monochromator | (Graphite) |
| Spinning | No |

*Note:
For some experiments, in order to improve the signal to noise ratio, the scan step time was increased to 5 or 12 seconds and/or a zero background slide was employed II. Differential Scanning Calorimetry (DSC)

The DSC cell/sample chamber was purged with 100 ml/min of ultra-high purity nitrogen gas. The instrument was calibrated with high purity indium. The accuracy of the measured sample temperature with this method is within about ±1° C., and the heat of fusion can be measured within a relative error of about ±5%.

Differntial scanning calorimetry was conducted on an Seiko Exstar DSC6200 instrument. For each crystalline form as follows: approximately 5 mg of material was weighed into an aluminium DSC pan and sealed non-hermetically with a pierced aluminium lid. The sample pan was then loaded into a Seiko DSC6200 (equipped with a cooler). The sample and reference were heated to ca. 270° C. (unless otherwise stated) at a scan rate of 10° C./min and the resulting heat flow response monitored. The heat flow, which was normalized by sample weight, was plotted versus the measured sample temperature. The data were reported in units of watts/gram ("W/g"). The plot was made with the endothermic peaks pointing down. The endothermic melt peak (melting point) was evaluated for extrapolated onset temperature.

III. Thermogravimetric Analysis (TGA)

The TGA instruments used to test the crystalline forms was a Seiko Exstar TG/DTA6200. Approximately 5 mg of material was weighed into an open aluminium pan and loaded into a simultaneous thermogravimetric/differential thermal analyser (TG/DTA) and held at room temperature. The sample was then heated at a rate of 10° C./min from 25° C. to 300° C. (unless otherwise stated) during which time the change in sample weight was recorded along with any differential thermal events (DTA). Nitrogen was used as the purge gas, at a flow rate of 100 cm3/min.

IV. Polarized Light Microscopy (PLM)

The presence of birefringence was determined using an Olympus BX50 polarizing microscope, equipped with a Motic camera and image capture software (Motic Images Plus 2.0). Images were recorded using a 20× objective lens.

V Ion Chromatography (IC)

Samples were first diluted in 10 mL water:methanol (5%) and then analysed for chloride content using the following experimental conditions:
Instrument: Dionex Chromatography System
Column: Dionex IonPac AS14A-5 μm, 3×150 mm
Guard Column: Dionex IonPac AG14A-5 μm, 3×30 mm
Mobile Phase: 15 mM Potassium Hydroxide
Flow Rate: 0.6 mL/min
Runtime: 25 minutes
Detector suppression: 50 mA, water regenerant as required
Column Temperature: 30° C.
Injection Volume: 25 μL VI High Performance Liquid Chromatography-Ultraviolet Detection (HPLC-UV)

To determine concentration, solutions were diluted in methanol; to determine purity, 2.7 mg material was dissolved in 1 mL methanol. The conditions listed below were then used.
Instrument: Agilent 1100
Column: Waters Symmetry C18 5μ 150×3.9 mm column
Column Temperature: 25° C.
Autosampler Temperature: Not controlled
UV wavelength: 254 nm
Injection Volume: 3 μL
Flow Rate: 1.2 mL/min
Mobile Phase A: 0.01% formic acid in water
Mobile Phase B: 0.01% formic acid in ACN
Gradient program:

| Time (minutes) | Solvent B [%] |
| --- | --- |
| 0.0 | 20 |
| 20.0 | 80 |
| 22.0 | 80 |
| 22.5 | 95 |
| 25.0 | 95 |
| 25.3 | 20 |
| 30.0 | 20 |

In one embodiment the present invention relates to a solid state form of ponatinib hydrochloride, comprising a crystalline form of ponatinib hydrochloride which may be characterized by a x-ray powder diffraction pattern (PXRD) comprising peaks at four or more 2θ values (CuKα λ=1.5419 Å) selected from the group consisting of 5.4, 10.0, 13.35, 14.07, 14.83, 17.57, and 26.02, measured at a temperature of about 22° C. and an x-ray wavelength, λ, of 1.5419 Å. This crystalline form of ponatinib hydrochloride is hereinbelow also referred to as form 1. Preferably, the crystalline form 1 of ponatinib hydrochloride may be characterized by a x-ray powder diffraction pattern comprising peaks at five or more 2θ values (CuKα λ=1.5419 Å) selected from the group consisting of 5.40, 10.0, 13.35, 14.07, 14.83, 17.57, and 26.02, at a temperature of about 22° C., preferably peaks at all of these 2θ values.

Figure 1:
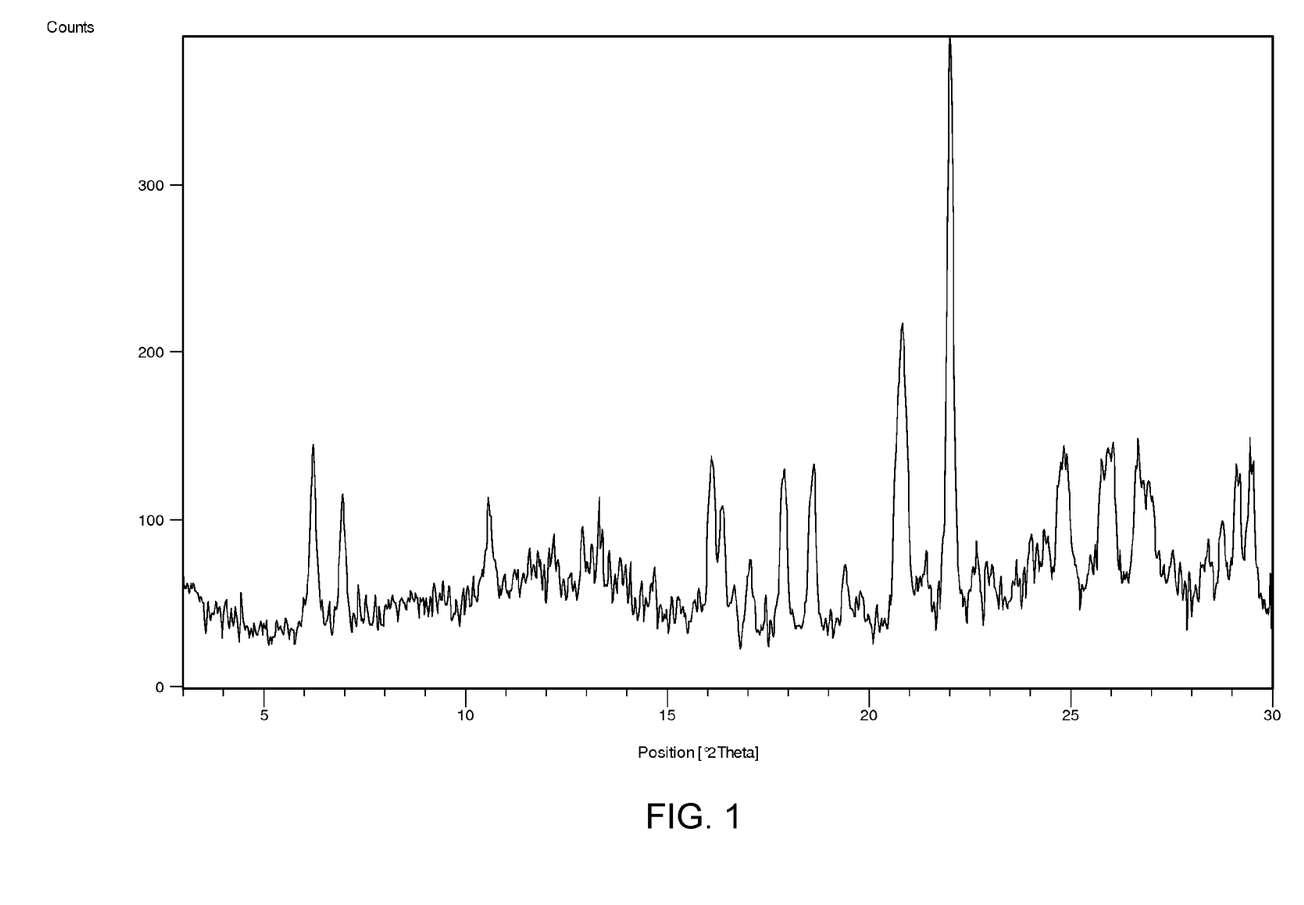
FIG. 1. illustrates the x-ray powder diffraction pattern of crystalline form 8 of ponatinib hydrochloride as obtained according to example 2c.

The present invention also provides crystalline form 1 of ponatinib hydrochloride having a X-ray diffraction spectrum substantially the same as the X-ray powder diffraction spectrum shown in FIG. 1.

The term "essentially the same" with reference to X-ray diffraction peak positions means that typical peak position and intensity variability are taken into account. For example, one skilled in the art will appreciate that the peak positions (2Θ) will show some inter-apparatus variability, typically as much as 0.2°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measure only.

The presence of more than one polymorph in a sample may be determined by techniques such as x-ray powder diffraction (PXRD) or solid state nuclear magnetic resonance spectroscopy. For example, the presence of extra peaks in the comparison of an experimentally measured PXRD pattern with a simulated PXRD pattern may indicate more than one polymorph in the sample. The simulated PXRD may be calculated from single crystal x-ray data. see Smith, D. K., "*A FORTRAN Program for Calculating X-Ray Powder Diffraction Patterns*," Lawrence Radiation Laboratory, Livermore, Calif., UCRL-7196 (April 1963) or TOPAS program (Total Pattern Analysis Solution, available through Brucker AXS Inc.).

A ponatinib hydrochloride crystal form may also be characterized by its water content. The present invention thus also relates to a crystalline form of ponatinib hydrochloride, wherein the crystalline form has a water content of at most 4%, such as of from 2% to 4%, preferably from 2.5% to 3.3%, when analyzed according to Karl Fischer. Preferably the crystalline form having a water content of from 2% to 4%, preferably from 2.5% to 3.3%, when analyzed according to Karl Fischer, is also characterized by having a x-ray powder diffraction pattern comprising peaks at five or more 2θ values (CuKα λ=1.5419 Å) selected from the group consisting of 5.40, 10.0, 13.35, 14.07, 14.83, 17.57, and 26.02, at a temperature of about 22° C., preferably peaks at all of these 2θ values.

In one embodiment of the present invention, crystalline form 1 of ponatinib hydrochloride is provided in substantially pure form. This crystalline form of ponatinib hydrochloride in substantially pure form may be employed in pharmaceutical compositions, in particular tablets, which may optionally include one or more other components selected, for example, from the group consisting of excipients, carriers, and one of other active pharmaceutical ingredients, active chemical entities of different molecular structure. A preferred pharmaceutical composition comprises ponatinib hydrochloride form I, lactose monohydrate, microcrystalline cellulose, sodium starch glycolate, colloidal silicon dioxide and magnesium stearate in a tablet core, followed by film coating with talc, polyethylene glycol, polyvinyl alcohol and titanium dioxide. The preparation of film coated tablets is well known in the art.

Preferably, the crystalline form 1 of ponatinib hydrochloride has substantially pure phase homogeneity as indicated by less than 10%, preferably less than 5%, and more preferably less than 2% of the total peak area in the experimentally measured PXRD pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

In one embodiment, a composition is provided consisting essentially of the crystalline form 1 of ponatinib hydrochloride. The composition of this embodiment may comprise at least 90 weight %, preferably at least 98 weight %, of the crystalline form 1 of ponatinib hydrochloride, based on the weight of ponatinib hydrochloride in the composition.

In another embodiment a composition is provided consisting essentially of the crystalline form 1 of ponatinib hydrochloride, which composition is having an ICH class 2 solvent content of less than 200 ppm, preferably of less than 20 ppm, more preferably of less than 5 ppm. This composition becomes available because the step of slurrying of form 8 in acetone or 2-propanol and conversion to form 1 removes ICH class 2 solvents.

In another embodiment the invention provides crystalline form 1 of ponatinib hydrochloride, which can be characterized by having a molar ratio of ponatinib:HCl of from 0.7 to 1.3, more preferably of from 0.8 to 1.2.

In another embodiment the invention provides crystalline form 1 of ponatinib hydrochloride, which can be characterized by a weight loss of at most 1.0%, preferably at most 0.2%, between 25° C. and 125° C., when measured by TGA.

In another embodiment the invention provides crystalline form 1 of ponatinib hydrochloride, which can be characterized by the absence of a local minimum indicative for an endothermic event between 55° C. and 70° C., when measured by DTA.

The invention further relates to crystalline form 1 of ponatinib hydrochloride, which can be characterized by having a molar ratio of ponatinib:HCl of from 0.7 to 1.3, more preferably of from 0.8 to 1.2, having a x-ray powder diffraction pattern comprising peaks at five or more 2θ values (CuKα λ=1.5419 Å) selected from the group consisting of 5.40, 10.0, 13.35, 14.07, 14.83, 17.57, and 26.02, at a temperature of about 22° C., preferably peaks at all of these 2θ values. In another preferred embodiment, the invention relates to a composition consisting essentially of the crystalline form 1 of ponatinib hydrochloride, which crystalline form 1 can be characterized by having a molar ratio of ponatinib:HCl of from 0.7 to 1.3, more preferably of from 0.8 to 1.2, and by having a x-ray powder diffraction pattern comprising peaks at five or more 2θ values (CuKα λ=1.5419 Å) selected from the group consisting of 5.40, 10.0, 13.35, 14.07, 14.83, 17.57, and 26.02, at a temperature of about 22° C, which composition is having an ICH class 2 solvent content of less than 200 ppm, preferably of less than 20 ppm, more preferably of less than 5 ppm.

The invention further relates to crystalline form 1 of ponatinib hydrochloride, which can be characterized by a weight loss of at most 1.0% between 25° C. and 125° C., when measured by TGA, having a x-ray powder diffraction pattern comprising peaks at five or more 2θ values (CuKα λ=1.5419 Å) selected from the group consisting of 5.40, 10.0, 13.35, 14.07, 14.83, 17.57, and 26.02, at a temperature of about 22° C., preferably peaks at all of these 2θ values. In another preferred embodiment, the invention relates to a composition consisting essentially of the crystalline form 1 of ponatinib hydrochloride, which crystalline form 1 can be characterized by a weight loss of at most 1.0%, preferably at most 0.2%, between 25° C. and 125° C., when measured by TGA, and by having a x-ray powder diffraction pattern comprising peaks at five or more 2θ values (CuKα λ=1.5419 Å) selected from the group consisting of 5.40, 10.0, 13.35, 14.07, 14.83, 17.57, and 26.02, at a temperature of about 22° C., preferably peaks at all of these 2θ values, which composition is having an ICH class 2 solvent content of less than 200 ppm, preferably of less than 20 ppm, more preferably of less than 5 ppm.

The invention further relates to crystalline form 1 of ponatinib hydrochloride, which can be characterized by the absence of a local minimum indicative for an endothermic event between 55° C. and 70° C., when measured by DTA, having a x-ray powder diffraction pattern comprising peaks at five or more 2θ values (CuKα λ=1.5419 Å) selected from the group consisting of 5.40, 10.0, 13.35, 14.07, 14.83, 17.57, and 26.02, at a temperature of about 22° C., preferably peaks at all of these 2θ values. In another preferred embodiment, the invention relates to a composition consisting essentially of the crystalline form 1 of ponatinib hydrochloride, which crystalline form 1 can be characterized by the absence of a local minimum indicative for an endothermic event between 55° C. and 70° C., when measured by DTA, and by having a x-ray powder diffraction pattern comprising peaks at five or more 2θ values (CuKα λ=1.5419 Å) selected from the group consisting of 5.40, 10.0, 13.35, 14.07, 14.83, 17.57, and 26.02, at a temperature of about 22° C., preferably peaks at all of these 2θ values, which composition is having an ICH class 2 solvent content of less than 200 ppm, preferably of less than 20 ppm, more preferably of less than 5 ppm.

Crystalline form 1 of ponatinib hydrochloride is useful in the treatment of neoplasms, cancers and hyperproliferative disorders e.g. chronic myelogenous leukemia (CML), in particular for the treatment of adults with chronic phase, accelerated phase, or blast phase chronic myeloid leukemia (CML) that is resistant or intolerant to prior tyrosine kinase inhibitor therapy, or Philadelphia chromosome positive acute lymphoblastic leukemia (Ph+ALL) that is resistant or intolerant to prior tyrosine kinase inhibitor therapy. Crystalline form 1 of ponatinib hydrochloride of the present invention may be used alone or in combination, or formulated with one or more excipients or other active pharmaceutical ingredients to provide formulations suitable for the treatment of the indications identified above.

Crystalline form 1 of ponatinib hydrochloride in substantially pure form shows much improved storage and handling properties compared to a composition comprising crystalline form 1 which has been prepared by direct crystallization from solution. For example, crystalline form 1 of ponatinib hydrochloride in substantially pure form can be stored for more than 7 days at 40° C. and 75% relative humidity without a significant decrease in polymorphic purity. This is contrary to crystalline form 1 of ponatinib hydrochloride obtained by direct crystallization from solutions.

The present invention also relates to a crystalline form 8 of ponatinib hydrochloride, which has been identified by the present inventors as a useful intermediate in the preparation of highly crystalline form 1 of ponatinib hydrochloride.

Thus, in one embodiment the present invention relates to a solid state form of ponatinib hydrochloride comprising a crystalline form of ponatinib hydrochloride which be characterized by a x-ray powder diffraction pattern (PXRD) comprising peaks at four or more 2θ values (CuKα λ=1.5419 Å) selected from the group consisting of 6.21, 10.58, 17.03, 18.62, 22.02, measured at a temperature of about 22° C. and an x-ray wavelength, λ, of 1.5419 Å. This crystalline form of ponatinib hydrochloride is hereinbelow also referred to as form 8. Preferably, the crystalline form 8 of ponatinib hydrochloride may be characterized by a x-ray powder diffraction pattern comprising peaks at five or more 2θ values (CuKα λ=1.5419 Å) selected from the group consisting of 6.21, 10.58, 17.03, 18.62, 22.02, 29.13, and 29.47, at a temperature of about 22° C., and preferably by comprising peaks at all of those 2θ values.

In a preferred embodiment the crystalline form 8 of ponatinib hydrochloride is provided in substantially pure form. This crystalline form of ponatinib hydrochloride in substantially pure form may be employed in the preparation of crystalline form 1 of ponatinib hydrochloride.

Preferably, the crystalline form 8 of ponatinib hydrochloride has substantially pure phase homogeneity as indicated by less than 10%, preferably less than 5%, and more preferably less than 2% of the total peak area in the experimentally measured PXRD pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

In one embodiment, a composition is provided consisting essentially of the crystalline form 8 of ponatinib hydrochloride. The composition of this embodiment may comprise at least 90 weight % of the crystalline form 8 of ponatinib hydrochloride, based on the weight of ponatinib hydrochloride in the composition.

The analytical methods described for characterization of form 1 above may also be used for characterization of crystalline form 8 of ponatinib hydrochloride.

The present invention also provides crystalline form 8 of ponatinib hydrochloride having a X-ray diffraction spectrum substantially the same as the X-ray powder diffraction spectrum shown in FIG. 1.

Ponatinib hydrochloride form 8 may also be characterized by its water content. The present invention thus also relates to a crystalline form of ponatinib hydrochloride, wherein the crystalline form has a water content of from 10% to 13%, preferably from 11% to 12%, when analyzed according to Karl Fischer.

In a further embodiment the present invention relates to a process for the preparation of ponatinib hydrochloride form 1, wherein ponatinib hydrochloride form 8 is slurried in a water soluble organic solvent for a time sufficient, such as from 6 h to 100 h, e.g. 12 h to 60 h, to allow conversion to ponatinib hydrochloride form 1. Preferred solvents for this conversion from form 8 to form 1 are organic solvents which are freely miscible with water at room temperature, such as freely miscible alcohols, e.g. methanol, ethanol, 1-propanol and 2-propanol, and freely miscible ketones or nitriles, e.g. aceton and acetonitrile. Preferred temperatures for this conversion are from 40° C. to the boiling point of the respective solvent, such as about 60° C. Care should be taken not to use too low a temperature for this step so as to avoid generation of a different crystal form.

The present invention also relates to crystalline ponatinib hydrochloride obtainable by slurrying ponatinib hydrochloride form 8 in 2-propanol at 60° C. and stirring the resulting slurry for 48 h.

In a further embodiment the present invention relates to a process for the preparation of ponatinib hydrochloride form 1, wherein
a composition comprising ponatinib hydrochloride form 1 is slurried in water for a time sufficient to allow conversion to ponatinib hydrochloride form 8 and
ponatinib hydrochloride form 8 is dehydrated for a time sufficient to cause conversion to ponatinib hydrochloride form 1.

Step b) is preferably carried out by a slurrying process in a water soluble organic solvent as described above and using times and temperatures as described above.

The present invention also relates to crystalline ponatinib hydrochloride obtainable by the process described in example 2c followed by the process described in example 3.

A skilled person will understand that R.H. or r.h. are abbreviations relating to the term "relative humidity".

The following non-limiting examples are illustrative of the disclosure.

EXAMPLES

Example 1

Preparation of Ponatinib hydrochloride (in EtOH/MeCN)

Figure 3:
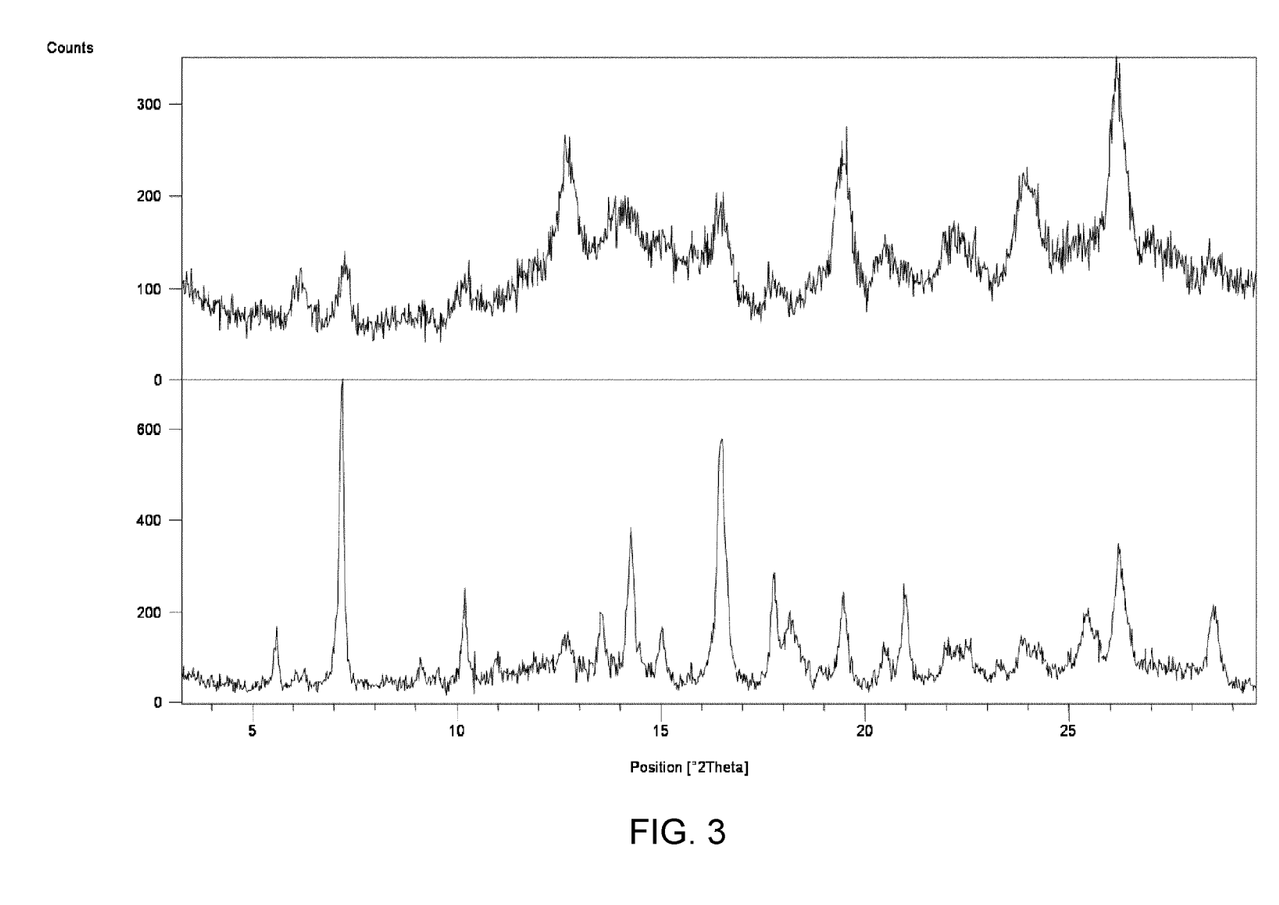
FIG. 3. compares the x-ray powder diffraction pattern of crystalline form 1 of ponatinib hydrochloride as obtained according to example 1 (top) with the x-ray powder diffraction pattern of crystalline form 1 of ponatinib hydrochloride as obtained according to example 3 (bottom; same as FIG. 2).

To a suspension of Ponatinib free base (4 g) in MeCN (20 ml) HCl in EtOH (10 ml) was added at 50° C. The mixture was stirred at this temperature for 1 h and then allowed to reach room temperature over 3 h. The resulted solid was collected by filtration and dried under reduced pressure at 40° C. over 48 h. Ponatinib hydrochloride form 1 was obtained as a solid (1.2 g, 28% yield). According to $^1$H NMR the product contains ca. 0.6% of ethanol. A crystal form showing some characteristic peaks which were not too well defined was found. DSC analysis showed multiple small endotherms with an onset of peaks at ca. 77.8° C., 113.7° C. and 166.7° C.; a possible exotherm with peak at ca. 221.9° C. and a final endotherm with onset of ca. 246.6° C. The corresponding XRD is shown in FIG. 3 top and was indicative of a sample comprising a significant amount of amorphous material.

Example 2a

A filtered solution of ponatinib HCl in acetonitrile/water (1:1) was allowed to slowly evaporate at ambient temperature. A hydrated crystal form 8 showing characteristic peaks at 6.21 and 10.5 2Theta was found. Approximately 11.4% water content was found by KF analysis. DSC analysis showed a large endotherm observed at onset ca. 78° C. (peak at 90° C.). The aqueous solubility of Form 8 was found to be 0.62mg/ml by HPLC analysis.

Example 2b

A filtered solution of ponatinib HCl in acetone/water (1:1) was allowed to slowly evaporate. A hydrated crystal form 8 showing characteristic peaks at 6.21 and 10.5 2Theta was found. Approximately 11.4% water content was found by KF analysis. DSC analysis showed a large endotherm observed at onset ca. 78° C. (peak at 90° C.). The aqueous solubility of Form 8 was found to be 0.62 mg/ml by HPLC analysis Example 2c Ponatinib HCl form 1 was slurried in water for 24 h at 22° C. A hydrated crystal form 8 showing characteristic peaks at 6.21 and 10.5 2Theta was found. Approximately 11.4% water content was found by KF analysis. DSC analysis showed a large endotherm observed at onset ca. 78° C. (peak at 90° C.). The aqueous solubility of Form 8 was found to be 0.62 mg/ml by HPLC analysis The corresponding XRD is shown in FIG. 1.

Example 3

Figure 2:
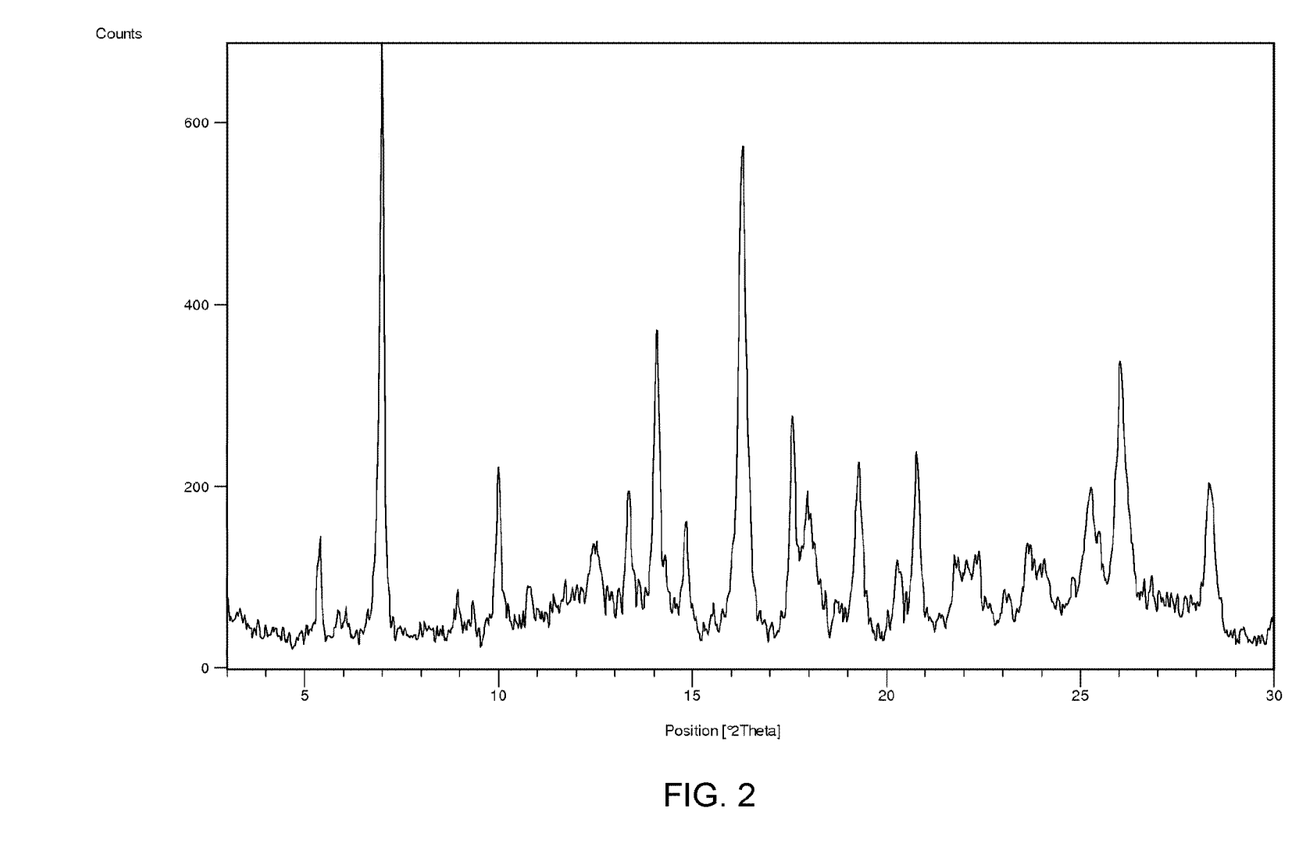
FIG. 2. illustrates the x-ray powder diffraction pattern of crystalline form 1 of ponatinib hydrochloride as obtained according to example 3.

Form 8 of ponatinib HCl was suspended in 2-propanol at 60° C. and the resulting slurry stirred for 48 h. The resulting solid was found to correspond to Form 1. However, compared to form 1 obtained by direct crystallization from solution, the sample from example 3 demonstrated a significantly higher degree of crystallinity. The corresponding XRD is shown in FIG. 2 and is repeated in FIG. 3, bottom panel, for the sake of better comparability.

Example 4

Recrystallization of Form 1

Approximately 200 mg of the dried ponatinib HCl form 1, prepared according to example 1, was slurried in 1-propanol at 60° C. and temperature cycled, with continuous agitation, in 4 hour cycles for a period of ca. 44 hours (slurries were held at 40° C. for 4 hours followed by a hold at ambient temperature for 4 hours, the cooling/heating rate after the 4 hour hold periods was ca. 1° C./min). The obtained solid ponatinib hydrochloride comprising crystalline form 1 was centrifuged, so that the excess solvent could be decanted, and the solid ponatinib hydrochloride was recovered and analyzed by XRPD, before drying briefly under nitrogen, and secondly under vacuum, for ca. 2 hours. The dried material was then analyzed by HPLC, for purity, IC, for chloride content, and also TG/DTA.

Example 5

Approximately 10 g of dried ponatinib HCl salt, prepared essentially according to example 1, but at correspondingly larger scale, was slurried in 250 mL 1-propanol in a 1l reactor vessel at 80° C. for ca. 20 minutes. The temperature was then reduced to 50° C. and the slurry was temperature cycled, with continuous agitation, in 2 hour cycles for a period of ca. 20 hours (slurries were held at 50° C. for 2 hours followed by a hold at ambient for 2 hours, the cooling/heating rate after the 2 hour hold periods was ca. 1° C./min) The obtained solid ponatinib hydrochloride comprising crystalline form 1 was then recovered by filtration and washed with ice-cold 1-propanol before drying under vacuum for ca. 24 hours. The quality of the resulting solid ponatinib hydrochloride was then assessed by XRPD, HPLC (chemical purity), TGA/DTA, DSC and Dynamic vapour sorption.

Analysis by XRPD showed that the material had crystallized successfully to Ponatinib HCl crystal Form 1, which was, however, not of high crystallinity. The obtained crystals were birefringent with a needle-like morphology. Analysis by HPLC indicated a purity of >99.9%. Analysis by IC indicated a 1.67:1 ratio of hydrochloride:freebase. The obtained material had a 1:0.1 ratio of Ponatinib:1-propanol, despite extensive drying. Thermal analysis of the material by TGA showed three weight losses: 2.33%, between 25° C. and ca. 120° C.; 3.15% between ca. 120° C. and 210° C.; 1.27% between ca. 210° C. and 258° C. Thermal analysis by DSC showed four endotherms: 96.4° C. (peak 111.9° C.), 163.2° C. (peak 172.0° C.), 194.3° C. (peak 210.5° C.), and 242.7° C. (peak 251.7° C.). The DVS isotherm showed a 1.2% change in mass between 10% and 70% RH, suggesting that the Form 1 material is also slightly hygroscopic.

Example 6

Approximately 10 g of Ponatinib HCl salt, prepared essentially according to example 1, but at correspondingly larger scale, was dissolved in 60 mL acetone:water (85%) in a 1l reactor vessel at 60° C. The resulting solution was stirred and cooled slowly from 60° C. to 5° C. over a period of 5 hours (0.18° C./min). Solid ponatinib hydrochloride comprising crystalline form 8 was then recovered by filtration and washed with ice-cold acetone:water (90%) before drying under ambient conditions for ca. 72 hours. The quality of the resulting solid was then assessed by XRPD, IC, TGA/DTA, DSC and dynamic vapour sorption.

Analysis by XRPD showed that the material had crystallized successfully to ponatinib hydrochloride crystal form 8. The obtained crystals appeared as large, birefringent rods. Analysis by IC indicated an about 1:1 ratio of hydrochloride:ponatinib. Thermal analysis of the material by TGA showed only one large weight loss: 11.12%, between 25° C. and ca. 120° C. Thermal analysis of the material by DTA showed three thermal events: 48.9° C. (peak ca. 69° C.): endotherm corresponding to the weight loss; 144.3° C. (peaks ca. 157° C., ca. 166° C., ca. 185° C.): possibly due to a form change; 257.4° C. (peak ca. 263° C.): exotherm, possibly due to onset of degradation. Thermal analysis of the material by DSC showed three endotherms below 100° C.: 36.8° C. (peak 42.5° C.), 60.6° C. (peak 62.7° C.), and 96.7° C. (peak 97.9° C.), possibly due to the dehydration of Form 8. Analysis by DVS showed that ponatinib hydrochloride crystal form 8 is a stable and reversible hydrate, picking up ca. 5 mole equivalents of water already at low humidity. The possible pentahydrate was also shown to be non-hygroscopic above 20% RH. Analysis by KF titration indicated a water content of about 14.4%. As 1 mole equivalent is equal to ca. 3%, this suggests that ponatinib hydrochloride is likely hydrated with ca. 5 mole equivalents of water and corroborates the DVS analysis.

Example 7

Approximately 500 mg Ponatinib hydrochloride crystalline form 8 was slurried in 1 mL 1-propanol and temperature cycled, with continuous agitation, in 4 hour cycles for a period of ca. 24 hours (slurries were held at 40° C. for 4 hours followed by a hold at ambient for 4 hours, the cooling/heating rate after the 4 hour hold periods was ca. 1° C./min). The slurry then was observed to have thickened, so a further 1.8 mL 1-propanol was added, and temperature cycling was continued. Solid material was then recovered by filtration and drying under vacuum for ca. 24 hours. The resulting solid ponatinib hydrochloride crystalline form 1 was then analyzed by XRPD, TGA, DTA, DSC and HPLC (chemical purity).

Analysis by XRPD showed that ponatinib hydrochloride crystalline form 1 which had been obtained via form 8 had increased in crystallinity compared to crystalline form 1 obtained from direct crystallization experiments, such as from example 5. Some diffraction peaks were also not present compared with Form 1 obtained by direct crystallization, possibly due to the removal of bound solvent/water. Thermal analysis by TGA showed a weight loss of less than 0.20%, likely due to unbound solvent/water, indicating that the conversion process from Form 8 had successfully removed bound water/solvent from Form 1. Thermal analysis by DTA showed one sharp endotherm, possibly due to a single melting event: 262.6° C. (peak ca. 261° C.). Also Analysis by DSC showed one sharp endotherm at 259.4° C. (peak ca. 263.6° C.), suggesting that the process of conversion had successfully improved crystallinity of ponatinib hydrochloride crystal form 1. Compared with ponatinib hydrochloride crystal form 1 obtained by direct crystallization (see e.g. example 5) a number of thermal events which in the direct crystallization example corresponded to the presence of possible bound solvent/water were not present in crystal form 1 obtained via form 8.

Example 8

In order to assess physical and chemical stability, Ponatinib HCl crystal form 1 obtained by direct crystallization according to example 4, and the crystalline ponatinib HCl Form 1 which was obtained via Form 8 according to example 7, were stored at 25° C./60%RH and 40° C./75% RH. After 1 week, the three samples were analysed by XRPD and HPLC (chemical purity). No changes in polymorphism were seen. The HPLC purity results of stability testing for each form are given in the table below:

| Stability testing conditions | Form I (direct crystallization) | Form 1 via form 8 |
|---|---|---|
| Initial purity | 99.9% | 99.8% |
| 25° C./60% r.h. | 99.6% | 99.8% |
| 40° C./75% r.h. | 99.3% | 99.8% |

Thus, the conversion of ponatinib hydrochloride crystalline form 8 to ponatinib hydrochloride crystalline form 1 produced ponatinib hydrochloride crystalline form 1 that was both of a higher degree of crystallinity and closer to a 1:1 ratio of hydrochloride to free base than ponatinib hydrochloride crystalline form 1 obtained by direct crystallization. Moreover, the stability studies indicate that ponatinib hydrochloride crystalline form 1 obtained via ponatinib hydrochloride crystalline form 8 was of higher chemical stability than ponatinib hydrochloride crystalline form 1 obtained by direct crystallization.

Example 9

Amorphous ponatinib HCl was stored at 40° C./75% r.h. for 7 days. The resulting material was analyzed for polymorphic form identity by XRD and was found to have partially converted to a hydrated crystal form showing characteristic peaks at 27.29, 28.85 and 29.82 2Theta Example 10a A solution of ponatinib HCl in acetone was kept at 2° C. for 4 days. The resulting slurry was filtered and the wet solid analyzed by XRPD. A solvated crystal form was found showing characteristic peaks at 24.28 and 26.18 2Theta. TG/DTA of the sample dried for 1 day showed ca. 4.4% weight loss <100° C. and ca. 5.4% weight loss between ca.100 and 200°

Example 10b

A solution of ponatinib HCl in acetone was diluted with t-butyl methyl ether. The resulting slurry was filtered and the wet solid analyzed by XRPD. A solvated crystal form was found showing characteristic peaks at 24.28 and 26.18 2Theta. TG/DTA of the sample dried for 1 day showed ca. 4.4% weight loss <100° C. and ca. 5.4% weight loss between ca. 100 and 200° C.

Example 11

A filtered solution of ponatinib HCl in acetonitrile/water (9:1) was allowed to slowly evaporate at ambient temperature. A hydrated crystal form showing characteristic peaks at 14.01 and 28.85 and 29.81 2Theta was found Example 12a A filtered solution of ponatinib HCl in acetonitrile/water (9;1) was crash cooled to 2° C. The resulting slurry was filtered A hydrated crystal form showing characteristic peaks at 9.22 and 24.09 2Theta was found.

Example 12b

A filtered solution of ponatinib HCl in acetonitrile/water (9;1) was crash cooled to −18° C. The resulting slurry was filtered A hydrated crystal form showing characteristic peaks at 9.22 and 24.09 2Theta was found.

Example 12c

A filtered solution of ponatinib HCl in acetonitrile/water (9;1) was diluted with t-butyl methyl ether. The resulting slurry was filtered. A hydrated crystal form showing characteristic peaks at 9.22 and 24.09 2Theta was found.

Example 12d

A filtered solution of ponatinib HCl in THF was diluted with t-butyl methyl ether. The resulting slurry was filtered. A hydrated crystal form showing characteristic peaks at 9.22 and 24.09 2Theta was found.

Example 13

Approximately 200 mg Ponatinib HCl salt according to example 1 was weighed into a vial and ca. 1 mL of Ethyl Acetate was added at 70° C. The resulting slurry was stirred and temperature cycled, with continuous agitation, in 4 hour cycles for a period of ca. 72 hours (slurry was held at 50° C. for 4 hours followed by a hold at ambient for 4 hours, the cooling/heating rate after the 4 hour hold periods was ca. 1° C./min) The slurry was observed to have thickened, so some material was removed from the vial and more of Ethyl Acetate added to produce a thinner slurry. Temperature cycling between 50° C. and ambient was then continued for a further 24 h. Solid material was then recovered and allowed to dry at ambient temperature prior to analysis by XRPD and PLM. A crystal form showing peaks at about 6.2, 12.2, 19.1 and 23.3 2Theta was found.

Example 14

Approximately 200 mg Ponatinib HCl salt according to example 1 was weighed into a vial and ca. 1 mL of a 1:1 mixture of N-methyl-2-pyrrolidone and tert-methyl butyl ether was added at 70° C. The resulting slurry was stirred and temperature cycled, with continuous agitation, in 4 hour cycles for a period of ca. 72 hours (slurry was held at 50° C. for 4 hours followed by a hold at ambient for 4 hours, the cooling/heating rate after the 4 hour hold periods was ca. 1° C./min). The slurry was observed to have thickened, so some material was removed from the vial and more of the 1:1 mixture added to produce a thinner slurry. Temperature cycling between 50° C. and ambient was then continued for a further 24 h. Solid material was then recovered and allowed to dry at ambient temperature prior to analysis by XRPD and PLM. A crystal form showing peaks at about 6.9, 10.0, 14.1 and 20.3 2Theta was found.

Example 15

Alternative Preparation of ponatinib HCl salt

Approximately 1 g of ponatinib free base was slurried in 2 ml 2-propanol and stirred at ambient temperature. 1 equivalent of a 7.85M propanolic HCl solution (239 µl), which had been prepared by bubbling HCl gas through 2-propanol until a constant chloride content had been achieved as judged by IS, was diluted in 2 ml 2-propanol and added to the slurry. Thickening of the slurry was observed, so a further 18 ml of 2-propanol was added and the slurry was stirred for 1 hour. Solid material was then recovered by filtration and analyzed by XRPD. A composition comprising ponatinib hydrochloride form 1 was obtained, essentially as in example 1.

What is claimed is:

1. A solid state form of ponatinib hydrochloride, consisting essentially of crystalline Ponatinib hydrochloride having a x-ray powder diffraction pattern comprising peaks at four or more 2θ values selected from the group consisting of 5.4±0.2, 10.0±0.2, 13.35±0.2, 14.07±0.2, 14.83±0.2, 17.57±0.2 and 26.02±0.2° (Cu Kα radiation at 22° C.).

2. The crystalline form of ponatinib hydrochloride according to claim 1, wherein the content of ICH class 2 solvent is less than 200ppm.

3. The crystalline form of ponatinib hydrochloride according to claim 1, which can be characterized by a weight loss of at most 0.2% between 25° C. and 125° C.

4. A tablet comprising the crystalline form of ponatinib hydrochloride according to claim 1, and a pharmaceutically acceptable carrier or diluent.

5. The tablet of claim 4, which is a film coated tablet.

6. The tablet of claim 5, wherein the tablet core comprises the crystalline form of ponatinib hydrochloride, lactose monohydrate, microcrystalline cellulose, sodium starch glycolate, colloidal silicon dioxide and magnesium stearate.

7. A solid state form of ponatinib hydrochloride, comprising a crystalline form having a x-ray powder diffraction pattern comprising peaks at four or more 2θ values selected from the group consisting of 6.21±0.2, 10.58±0.2, 17.03±0.2, 18.62±0.2, 22.02±0.2, 29.13±0.2, 29.47±0.2° (Cu Kα radiation at 22° C.).

8. The crystalline form of ponatinib hydrochloride according to claim 7, having an X-ray diffraction spectrum substantially the same as the X-ray powder diffraction spectrum shown in FIG. 1.

9. A composition comprising at least 90 weight % of the crystalline form according to claim 1, based on the weight of the composition.

10. A crystalline form of ponatinib hydrochloride obtainable by slurrying a crystalline form of ponatinib hydrochloride according to claim 7 in a water miscible organic solvent, optionally by slurrying the crystalline form in 2-propanol at 60° C. and stirring the resulting slurry for 48h.

11. The crystalline form of ponatinib hydrochloride according to claim 1, having an X-ray diffraction spectrum substantially the same as the X-ray powder diffraction spectrum shown in FIG. 2.

12. The crystalline form of ponatinib hydrochloride according to claim 1, having a x-ray powder diffraction pattern comprising an additional peak at the 2θ value 6.99±0.2° (Cu Kα radiation at 22° C.).

13. The crystalline form of ponatinib hydrochloride according to claim 10, further comprising drying under a nitrogen purge to afford the crystalline form.

* * * * *